(12) United States Patent
Wurzbacher et al.

(10) Patent No.: US 7,326,305 B2
(45) Date of Patent: Feb. 5, 2008

(54) SYSTEM AND METHOD FOR DECAPSULATING AN ENCAPSULATED OBJECT

(75) Inventors: Ray R. Wurzbacher, Palm Bay, FL (US); Stephen B. Walchli, Palm Bay, FL (US)

(73) Assignee: Intersil Americas, Inc., Milpitas, CA (US)

( * ) Notice: Subject to any disclaimer, the term of this patent is extended or adjusted under 35 U.S.C. 154(b) by 261 days.

(21) Appl. No.: 10/768,942

(22) Filed: Jan. 30, 2004

(65) Prior Publication Data

US 2005/0167400 A1 Aug. 4, 2005

(51) Int. Cl.
*B08B 3/04* (2006.01)
(52) U.S. Cl. .......................... 134/19; 134/26
(58) Field of Classification Search ............. 134/100.1, 134/102.1, 102.2, 105, 108
See application file for complete search history.

(56) References Cited

U.S. PATENT DOCUMENTS

| | | | | |
|---|---|---|---|---|
| 3,084,076 A | * | 4/1963 | Loucks et al. | 134/22.1 |
| 3,489,608 A | * | 1/1970 | Jacobs et al. | 134/25.4 |
| 3,625,763 A | * | 12/1971 | Melillo | 134/38 |
| 3,990,462 A | * | 11/1976 | Elftmann et al. | 134/102.1 |
| 4,682,615 A | * | 7/1987 | Burkman et al. | 134/102.2 |
| 5,252,179 A | * | 10/1993 | Ellerson et al. | 216/90 |
| 5,395,482 A | * | 3/1995 | Onda et al. | 216/73 |
| 5,766,496 A | * | 6/1998 | Martin | 216/56 |
| 5,896,875 A | * | 4/1999 | Yoneda | 134/102.3 |
| 5,939,139 A | * | 8/1999 | Fujimoto | 427/240 |
| 6,200,387 B1 | * | 3/2001 | Ni | 118/722 |
| 6,732,911 B2 | * | 5/2004 | Matsuki et al. | 228/219 |
| 7,022,244 B2 | * | 4/2006 | Sakaida et al. | 216/2 |

FOREIGN PATENT DOCUMENTS

| | | | |
|---|---|---|---|
| JP | 62-296527 | * | 12/1987 |
| JP | 9-199834 | * | 7/1997 |
| TW | 463340 | * | 11/2000 |

* cited by examiner

*Primary Examiner*—Frankie L. Stinson

(57) ABSTRACT

A system and method for the selective etching or removal of encapsulating material from an encapsulated object, such as a semiconductor, includes depositing an encapsulant-removal agent, such as a solvent or acid, onto the surface of the object. A flow of heated gas, such as an inert gas, is directed onto the deposited agent to effect the heating thereof and promote the removal of the encapsulating material. In general, the flow of heated gas is sufficient to cause the formation of a depression or depression-like concavity in the surface of the removing agent to promote the removal process. In a preferred embodiment, a pipe is provided with an internal heater to heat the gas flow there through and a nozzle at one end to direct the gas flow toward and onto the deposited removal agent.

15 Claims, 2 Drawing Sheets

SYSTEM AND METHOD FOR DECAPSULATING AN ENCAPSULATED OBJECT

BACKGROUND OF THE INVENTION

The present invention relates to decapsulation of an encapsulated object. The invention includes a system and method for etching away ("decapsulation") the plastic or epoxy material encapsulating an object, such as a semiconductor or integrated circuit component, for purposes that can include visual inspection and/or failure analysis.

Plastics and plastic-like materials have been used to encapsulate electrical components, including semiconductor devices, for many years. To provide a plastic packaging around an object epoxy resin is typically molded around the object. For example, epoxy resin is molded around a semiconductor die and the lead frame on which the semiconductor die is attached, including the bonding wires or other connections between the die and the lead frame. Once encapsulated, however, an internal visual inspection or internal probing of the interior of the encapsulated object is not possible. Consequently, removal of the epoxy is often desired to allow for inspection or testing of the encapsulated object, particularly in the case of failure analysis.

Typically, the component to be decapsulated is heated on a hotplate or other heating device. The type of acid and etch temperature is selected based on the properties of the material to be etched, since it is known in the art that different encapsulation materials react with some acids better than others. Suitable acids include fuming sulfuric or fuming nitric acid. Fuming sulfuric acid requires a high temperature of approximately 300 degrees Celsius whereas fuming nitric acid requires a high temperature in the approximately 100 degree Celsius range.

Commonly, concentrated acids, such as sulfuric acid and nitric acid, or other solvents for the specific resin have been employed, depending on the type of resin to be removed. Significant amounts of acid are dropped onto the heated component, which causes a reaction with the encapsulating material that removes the encapsulating material from the object. Waste material from the component is then rinsed away using acetone or another suitable procedure. Then the process is repeated, with the heating of the package and then more acid being dropped on the area of the encapsulating material to be removed. The procedure is repeated until the object is decapsulated; in this example, the semiconductor die and/or lead frame connections are exposed.

One problem experienced in the commonly used procedure is that heating the semiconductor component may alter its physical and electrical characteristics. This is particularly true if the component has been attached to a printed circuit board since heating the entire board can easily damage or alter the characteristics of the board and surrounding components.

Accordingly, it is an object of this invention to provide a controllable method of selectively removing the encapsulating material including system and method for the "spot" removal of the encapsulating material from a selected area of the encapsulated object.

SUMMARY OF THE INVENTION

The present invention provides a system and method for decapsulating an encapsulated component including the controlled selective thermal decapsulation of an object ("device under test"), such as a semiconductor component.

The preferred embodiment provides a controllable high temperature focused flow of heated inert gas directed at a substantially hemispherically shaped formation of an acid, formed by placing one to any number of drops of acid necessary to cover the area to be decapsulated, on the encapsulating material of the device under test. Any amount of acid may be used so long as the hemispherical or dome-like shape is maintained.

Any inert gas, such as nitrogen or argon is suitable. Other gases or combination of gases may be used, however, keeping moisture out of the etch process is desired in those situation where any aluminum or aluminum alloys are or may be present in the area being etched.

Intuitively, directing a heated inert gas onto a hemisphere of acid might blow or otherwise force the acid off the plastic package or otherwise cause it to react with the encapsulating material in an uncontrolled fashion. However, if the flow of the inert gas is adjusted to the point where it causes a depression or depression-like concavity to form in the center of the hemisphere or hemispheric-like formation of acid, the reaction with the encapsulating material occurs primarily under the depression or depression-like concavity, thus allowing one to observe, direct, and control the reaction to those parts of the encapsulating material desired to be etched.

The preferred embodiment of one version of the system consists of a pipe containing an electrically controlled heater core attached to a thermal control unit. A flow of nitrogen gas, the rate of which is controlled by a connected flow meter, is forced into the pipe and is heated therein by the heater core. As the nitrogen exits the pipe containing the heater core, a thermo-couple or similar temperature sensor connected to the thermal control unit measures the temperature of the nitrogen. Thus the temperature of the nitrogen can be measured, adjusted, and maintained as desired.

If desired, the outlet end of the pipe can be adjustable or provided with a removable end cap so that different end caps with differently sized exit aperture nozzles can be used.

The pipe may be manipulated manually or be mounted on a stand that allows for the adjustment of the height or spacing between the nozzle and the device under test being decapsulated.

To decapsulate a device under test using the system, one or more drops of acid are placed on the material encapsulating the device under test to create a hemispheric-like acid formation. Using the system, heated nitrogen is directed toward the hemisphere or hemispheric-like formation of acid until the normally dome-shaped hemisphere or hemispheric-like formation of acid exhibits a depression or depression-like concavity.

Using the method and the system combined, the reaction of the acid with the encapsulating material is controlled by adjusting the temperature of the nitrogen, the flow rate of the nitrogen, and adjusting the distance or spacing from the source of the heated nitrogen to the hemisphere or hemispheric-like formation of acid.

BRIEF DESCRIPTION OF THE DRAWINGS

The objects and advantages of the present invention will become more readily apparent to those ordinarily skilled in the art after reviewing the following detailed description and accompanying drawing, wherein.

DETAILED DESCRIPTION OF THE PREFERRED EMBODIMENT

Figure 1:
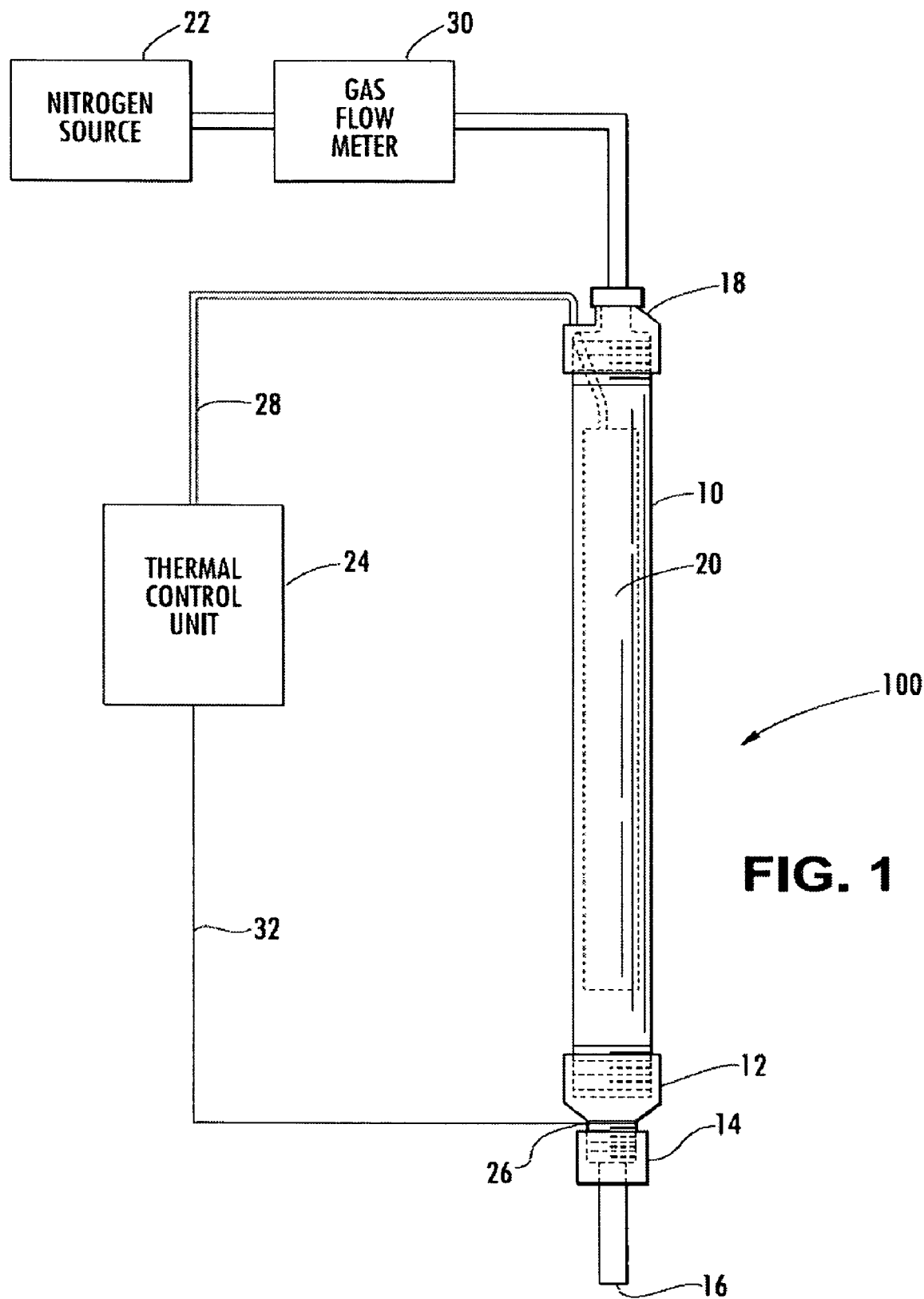
FIG. 1 is a diagram of a version of the decapsulation system.

FIG. 1 illustrates a decapsulation system in accordance with the present invention and referred to by the general reference numeral 100. The decapsulation system 100 of the preferred embodiment includes a 3/8 inch pipe 10 five inches long and threaded on both ends. The pipe 10 can be fabricated from any suitable material, including metal; in the case of the preferred embodiment the pipe is fabricated from brass.

A gas flow, such as nitrogen gas, is introduced into the pipe 10 through an intake end cap 18 and controlled by a flow meter 30. Positioned inside the pipe 10 is a heater core 20 connected externally 28 to a thermal control unit 24. In the case of the preferred embodiment the heater core is a 300-watt heater core.

A thermal control unit 24 is also connected 32 to a device for measuring the temperature of the nitrogen gas flow 26. In the case of the preferred embodiment, a thermo-couple 26 or similar device in an exhaust end cap 12 allows the temperature of the nitrogen to be monitored and controlled. In the preferred embodiment the exhaust end cap 12 includes a reducer from 3/8 inch diameter to 1/4 inch diameter to allow for the attachment of a smaller exhaust nozzle 14. The exhaust nozzle should be replaceable or adjustable to allow for several sizes of exit apertures, allowing for increased accuracy of the flow of the heated nitrogen at the output 16.

While the system 100 as shown in FIG. 1 can be manipulated by hand, it may also be mounted on an adjustable stand (not shown) with at least a Z-axis control, for example a z-axis control structure found on a microscope. Such a mounting allows for a more stable and precise adjustment of the distance between the exhaust nozzle 14 and the surface of the object being decapsulated.

Figure 2A:
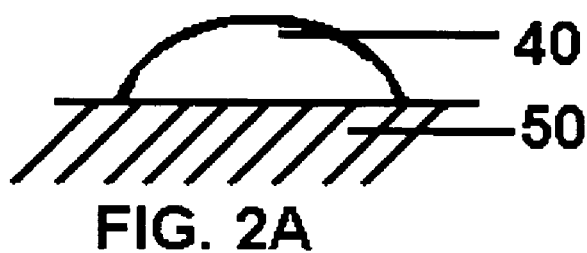
FIG. 2A is a detailed view, in side-elevation, of a hemisphere or hemispheric-like formation of acid on the surface of an encapsulated device under test.

The preferred method of using the present version of the system 100 is to locate it over the component to be decapsulated. As shown in FIG. 2A, a hemispheric deposit of acid 40 is placed on the encapsulation material 50.

The hemispheric deposit of acid 40 is formed by placing one to any number of drops of acid necessary to cover the area to be decapsulated. Any amount of acid may be used so long as the hemispherical or dome-like shape is maintained.

The type of acid and etch temperature is selected based on the properties of the material to be etched, since it is known in the art that different encapsulation materials react with some acids better than others. Suitable acids include, for example, fuming sulfuric or fuming nitric acid.

Figure 2B:
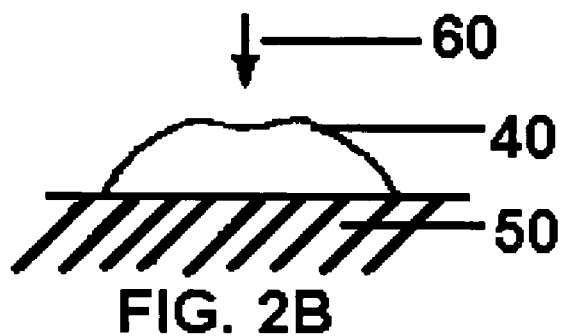
FIG. 2B is a view, similar to FIG. 2A, showing the formation of a depression or depression-like concavity in the hemisphere or hemispheric-like formation of acid as a result of the directed flow of heated gas.

As shown in FIG. 2B, a flow of heated nitrogen 60 from the system 100 is directed toward the hemispheric deposit of acid 40 until a depression or depression-like concavity is formed in the hemisphere or hemispheric-like formation of acid 40. Heating the acid 40 with the heated nitrogen 60 and creating the depression or depression-like concavity causes the acid under the depression or depression-like concavity to be preferentially or locally heated and to react with the encapsulation material 50 locally "wetted" by the hemisphere or hemispheric-like formation 40. Because the location of the reaction is substantially restricted to the area under the depression or depression-like concavity in the hemisphere or hemispheric-like formation of acid 40, as shown in FIG. 2C, the amount of material etched away is easily controlled without disturbing other adjacent or nearby areas, such as the periphery of the semiconductor component, the lead frame and the bond wires.

Figure 2C:
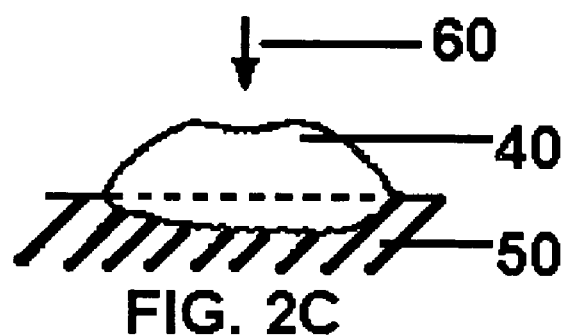
FIG. 2C illustrates, in an exemplary manner, the selective etching that occurs under the heated hemisphere or hemispheric-like formation of acid.

As best shown in FIG. 2C, once the heated acid begins etching the surface "wetted" by the hemisphere or hemispheric-like formation 40, a pit is formed which serves to further confine the acid in the desired area. The reaction of the acid 40 and the encapsulation material 50 may be controlled by adjusting the temperature of the nitrogen 60, the flow rate of the nitrogen 60, and adjusting the distance from the source of the heated nitrogen 60. In addition, selection of the appropriate size exhaust nozzle 16 allows the area of the reaction to be controlled. Hence, a controlled area of encapsulation material can be selectively etched. This is particularly useful when decapsulating very small semiconductor components.

Also, because the area of reaction is limited, very little waste material is produced. If necessary, any residue from the reaction that needs to be removed may usually be removed with a single wash with acetone or other cleansing fluid upon completion of the procedure.

The present version of the invention 100 is not limited to decapsulation of an un-mounted encapsulated component, such as a single semiconductor. Because the present version of the invention allows for a controlled area of encapsulation material to be selectively etched away, it is useful for decapsulating a semiconductor component mounted on a printed circuit board. If there is a concern that the reaction of the acid may splash or otherwise damage surrounding areas or components on the printed circuit board, such surrounding area can be brushed with photo-resist or conformal coating.

Figure 2D:
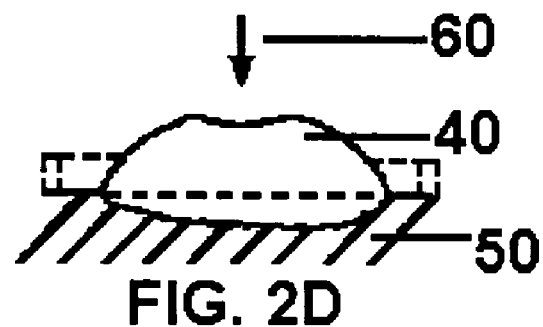
FIG. 2D shows the placement of an optional "dam" (dotted-line illustration) surrounding the to-be-etched area.

If desired, and as shown in FIG. 2D, a dam or guard can be positioned to surround the hemisphere or hemispheric-like formation to prevent unexpected spreading or migration.

In the embodiment shown, the electrical heater is positioned within the pipe; as can be appreciated, other variations are possible. For example, a separate heater unit may be provided downstream or upstream of the flow controller to heat the gas flow in advance of its entry into the delivery pipe.

Although the present invention has been described in considerable detail with reference to certain preferred versions thereof, other versions are possible. Therefore, the spirit and scope of the appended claims should not be limited to the description of the preferred versions contained herein.

What is claimed is:

1. An encapsulation removal method for removing a portion of an encapsulating material from an encapsulated integrated circuit comprising the steps of:

depositing a selected volume of a liquid encapsulant-removing agent on a selected surface area of the surface of an encapsulated integrated circuit, the selected volume of the liquid encapsulant-removing agent sufficient to form a shape-sustaining and substantially position-maintaining deposit on the selected surface area;

subjecting the deposited liquid encapsulant-removing agent to a flow of a heated gas sufficient to heat the deposited liquid encapsulant-removing agent to cause the so-heated liquid encapsulant-removing agent to remove at least a portion of the encapsulating material in contact with the so-heated liquid encapsulant-removing agent in the selected surface area, the flow of heated gas insufficient to cause the encapsulant-removing agent to migrate from its initially deposited position on the surface of the integrated circuit and the flow of heated gas and the encapsulated integrated circuit characterized by the substantial absence of relative movement therebetween during the heating of the deposited liquid encapsulant-removing agent.

2. The method of claim 1, wherein the liquid encapsulant-removing agent is selected from solvents that will remove the encapsulating material when heated.

3. The method of claim 1, wherein the liquid encapsulant-removing agent is selected from a group of acids that will remove the encapsulating material when heated.

4. The method of claim 3, wherein the acid is selected from a group of acids including nitric acid or sulfuric acid.

5. The method of claim 1, wherein the gas is a substantially insert gas.

6. The method of claim 1, wherein the gas is nitrogen or argon or a mixture thereof.

7. The method of claim 1, wherein the gas is substantially moisture-free.

8. The method of claim 1, wherein the removing agent is deposited so as to form a substantially shape-sustaining hemispheric or hemispheric-like formation on the surface of the encapsulated integrated circuit.

9. The method of claim 8, wherein the removing agent is deposited by placing one or more drops or droplets on the surface of the encapsulated integrated circuit to form the substantially shape-sustaining hemispheric or hemispheric-like formation.

10. The method of claim 8, wherein the flow of heated gas is sufficient to form a depression or depression-like indentation in the formation.

11. The method of claim 10, wherein the removing agent is an acid selected from a group of acids including nitric acid or sulfuric acid.

12. The method of claim 1, further comprising a temperature sensor for sensing the temperature of the heated gas.

13. The method of claim 12, further comprising a means for controlling the temperature of the heated gas.

14. The method of claim 13, wherein the temperature of the heated gas is controlled between approximately 100 and 300 degrees Celsius.

15. The method of claim 1, further comprising a flow controller for controlling the flow rate of the heated gas.

* * * * *